United States Patent [19]

King

[11] Patent Number: 4,575,208
[45] Date of Patent: Mar. 11, 1986

[54] LENS MOUNTED LIGHT SYSTEM

[76] Inventor: Bedford G. King, 526 N. Third St., Bardstown, Ky. 40004

[21] Appl. No.: 582,007

[22] Filed: Feb. 21, 1984

[51] Int. Cl.³ .......................... G03B 15/02; A61B 3/10
[52] U.S. Cl. ...................... 354/126; 354/62; 354/295; 351/206; 362/12
[58] Field of Search ....... 354/62, 126, 145.1, 354/149.11, 295; 351/206, 207, 208; 362/3, 11, 12

[56] References Cited

U.S. PATENT DOCUMENTS

| | | | |
|---|---|---|---|
| 2,400,483 | 5/1946 | Cameron | 354/62 |
| 2,501,405 | 3/1950 | Noel | 354/126 |
| 3,388,646 | 6/1968 | Sullivan | 351/206 |
| 4,061,423 | 12/1977 | Pomerantzeff | 351/206 |
| 4,184,752 | 1/1980 | Richards et al. | 351/206 |
| 4,394,074 | 7/1983 | McMahon et al. | 351/206 |
| 4,423,470 | 12/1983 | Naito et al. | 354/126 |

FOREIGN PATENT DOCUMENTS 261091  3/1964  Australia ..................... 354/62

Primary Examiner—A. A. Mathews

[57] ABSTRACT

A cap arrangement having an aperture for use with a camera lens where the cap includes a focusing light and a light flash device to facilitate macro photographic procedures.

4 Claims, 8 Drawing Figures

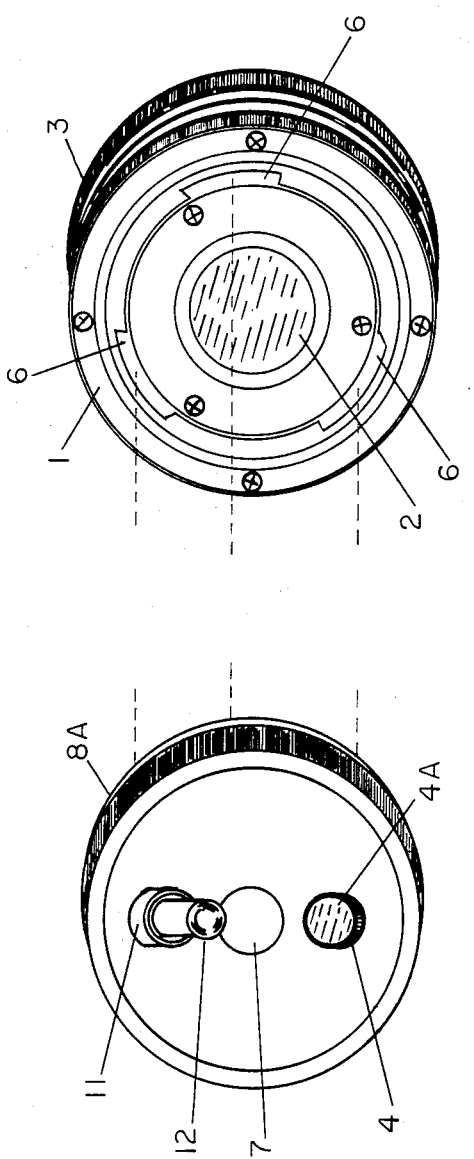
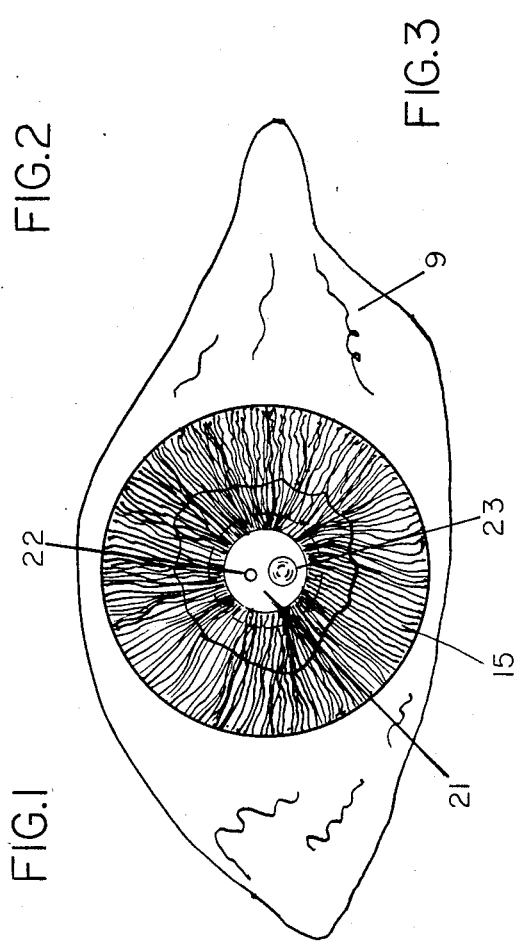

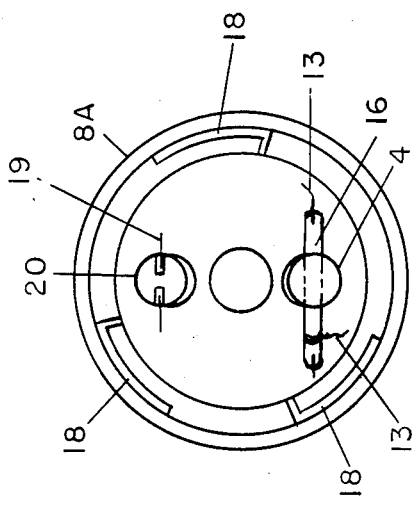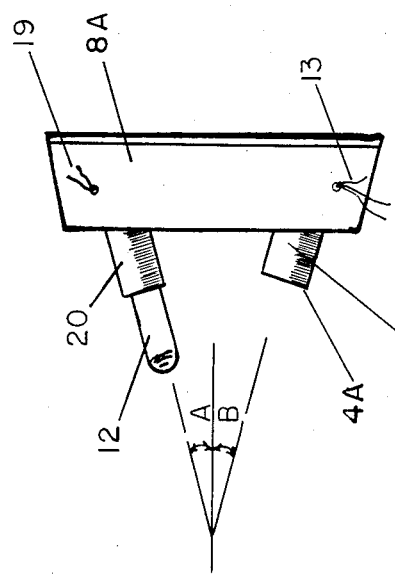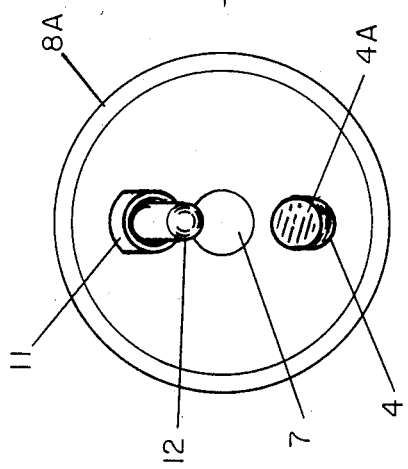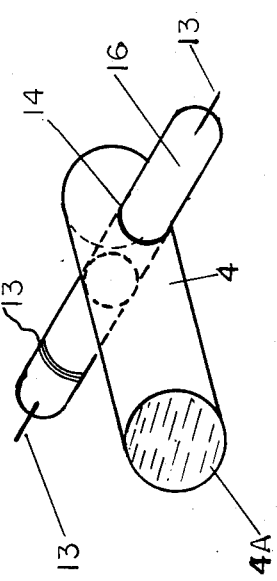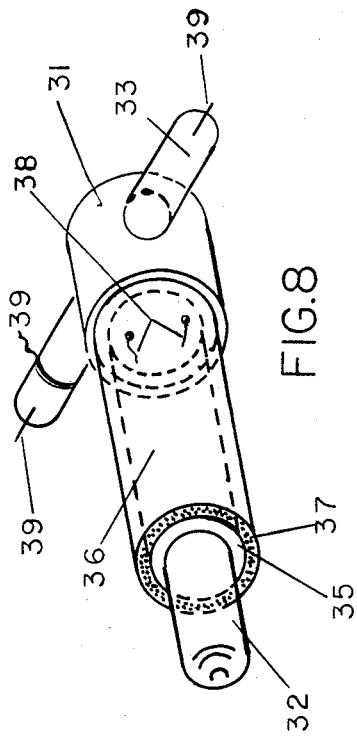

LENS MOUNTED LIGHT SYSTEM

BACKGROUND OF THE INVENTION

The present invention relates principally to illumination devices for use in macrophotography, which are particularly useful in photography of the eye and even more particularly photography of the iris, sclera, cornea, pupil and lens of the eye.

The iris of the eye, which resembles a moveable curtain is composed of an infinite number of very fine, small, nerve filaments which receive impulses from every nerve center of the body. Accordingly the iris provides a visible outward terminus of the entire nervous system enabling the most exact analysis and/or diagnosis of the general condition of the body. For example, such analysis is utilized in studies of the vascular and lymphatic systems as well as the individual parts and organs of the body. The analysis usually is conducted by making a photograph of the iris of the eye. Such photography is in many instances tedious and exacting because of the reflective nature of the eye and it is necessary to obtain a clear photograph without the obliteration which would result from reflected light.

Therefore it is necessary that appropriate lighting be provided to illuminate the portion of the eye to be photographed without compromising the photograph by reflection of light in the iris that don't belong there; which actually obscure parts of the iris.

Certain prior art arrangements are known for providing illumination for recording of fundus disorders or other eye condition but such prior art devices have in general been complex, expensive, and difficult to operate. Further the prior art devices have not provided the ocular illumination which is required to enable the photography of the internal portions of the eye without reflection of light from the strobe which distort or obliterate the essential elements being photographed.

One prior art arrangement is a Nikon TM medical Nikkor 120 mm f41F which provides a self contained focusing light with a ring strobe light. However, the device tends to obliterate the area being photographed because of the circular size of the light pattern emitted from the device.

Likewise Olympus TM Optical Company of Tokoyo, Japan provides a macro photo light which like the Nikkor medical light provides a ring of light and is not entirely suitable for use as a light source for the eye for the same reasons.

Other known prior art arrangements include the device taught by U.S. Pat. No. 4,394,074 McMahon which provides a two separate fiber optic light wands that are arranged to be positioned in close proximity to the eye and used to shape and accommodate the radius in the configuration of the eye so that most of the light pattern is presumably located in the iris of the eye.

Another prior art arrangement is shown in U.S. Pat. No. 4,061,423 Pomeratzeff which like the previously discussed reference teaches a fiber optic source which is positioned against the eye.

Finally, U.S. Pat. No. 4,184,752 Richards provides an arrangement including an incandescent focusing light of low intensity for illumination of the objects to be examined and a strobe tube which provides a short duration high intensity flash illumination. However, the arrangements shown in the later noted patent provides for a movement of the lighting systems between the focusing and the actual photography and do not permit through the lens focusing with the incandescent light carried by the lens member. The arrangement is somewhat complex and expensive and would not provide the advantages inherent in devices within the scope of the present invention.

No prior art arrangement is known where a cap member is attached to a selected lens or macro photography. Fluorescent focusing light is carried by the cap and a fiber optic tube extends out of the cap with a strobe tube carried diametrically across the tube to provide a flash through the tube when a strobe light is actuated.

SUMMARY OF THE INVENTION

The present invention provides a new, straightforward and inexpensive arrangement to facilitate macro photography and particularly to provide illumination in the photographic procedures for analysis of the iris and associated portions of the eye.

Devices within the scope of the present invention provide a cap which is attached to a macro lens suitable for macro photography. The lens arrangement is a wide angle lens reverse mated which then becomes a close up lens. This simple lens arrangement has been found to be entirely satisfactory to accomplish the objective of the present invention when utilized with a light source in accordance with the present invention.

Briefly, the light source within scope the present invention includes a cap member which is located over the lens to be used for the macro photographic procedure where an aperture is provided through the center of the cap in alignment with the lens aperture. An incandescent light is provided on the cap adjacent the aperture and is utilized to provide a focusing light for the subject to be photographed. A fiber optic tube is provided to extend through the cap adjacent the aperture and carries a strobe light so that after focusing is accomplished by use of the incandescent lamp, the strobe light is actuated in conjuction with the actuation of the camera shutter so that the illumination of the strobe light passes through the fiberoptic tube and to the area to be photographed. Because the fiberoptic tube directs a beam of light into the pupil of the iris or sclera the iris or subject is photographed without distortion or reflection of light that doesn't belong there.

The strobe electronics are known to those skilled in the electronics art and are not shown. Furthermore, any miniature electronic strobe can be utilized within the invention.

Examples in accordance of the present invention are shown in the accompanying Figures but it will be understood that various other arrangements within the scope of the present invention will occur to those skilled in the art upon reading the disclosure setforth hereinafter.

BRIEF DESCRIPTION OF THE DRAWINGS

In the examples of the present invention discussed hereinafter;

FIG. 1 an exploded perspective view of an arrangement within the scope of the present invention;

FIG. 2 an exploded perspective view of the lens system reverse mated;

FIG. 3 is a view of the eye showing the focus light and strobe light in the pupil.

FIG. 4 is a front view of a lens cap arrangement within the scope of the present invention;

FIG. 5 is a side view of the arrangement shown in FIG. 4;

FIG. 6 is a rear view of the arrangement shown in FIG. 4;

FIG. 7 is an exploded pictorial view of a strobe light and fiberoptic cylinder within the scope of the present invention; and FIG. 8 is an illustration of an alternative arrangement within the scope of the present invention for utilization of a lens cap utilizing the fiber optic sleeve.

DETAILED DESCRIPTION OF THE DRAWINGS

Referring first to FIG. 1 which illustrates in exploded arrangement within the scope of the present invention, a lens 1 is provide which can be a 24 to 28 mm wide angle lens, as known in the art, having a lens 2. A reverse mate connection 3 is carried by the lens in reverse orientation to a camera (not shown). The lens is a wide angle lens and by reverse mating, as also known in the art, the lens is converted to a photographic close up lens. A lens cap 8A, as shown in FIG. 1, is provided to be received in three connector lugs 6 of lens 1. Lens cap 8A has a central aperture 7 in alignment with the lens 2 of the lens assembly 1 so that the image to be photographed pass through aperture 7 to lens 2, other lens, and then to the camera body, as known in the art. A low intensity, low voltage light 12 is provided which burns continuously during the photographic procedure, as described hereinafter, to facilitate focusing of the lens assembly 1 on the object to be photographed. For purposes of the description of the present invention it will be assumed that the subject to be photographed is an eye 9, a segment of which is shown in FIG. 3.

An aperture is provided in lens cap 8A, as shown, to receive a fiber optic cylinder 4 which extends therethrough and is directed in the general area of the subject to be photographed, in this case the iris 15 of eye 9. The unit is assembled with the lens cap, shown in FIG. 1 and FIG. 6. Proper focal distance is selected in accordance with the focal distance of the lens selected. FIG. 5 is a side view showing the lens cap 8A with the focusing light 12 and the fiber optic, for example acrylic, tube 4 extending outwardly therefrom. It will be understood that the ends of fiber optic tube 4, for example acrylic, are polished at the end 4A to provide the maximum degree of light transmission. Power leads 13 are provided to provide a instantaneous electrical burst to a strobe light 16, as shown in FIG. 7, which is located within the lens cap where the leads 13 are connected to the miniature electronic strobe electronics. The outer surface 4A of the fiber optic cylinder or acrylic tube 4 are polished, as previously described, and the strobe light tube 16 extends through an aperture 14 in tube 4 so that light obtained upon the light burst from the strobe light 16 passes outwardly through the end 4A of tube 4 toward the subject or object to be photographed to provide the lighting necessary for device. An arrangement of the rear side of the lens cap 8A, as shown in FIG. 6, where mating lugs 18 are shown to mate with the lugs 6 of lens assembly. Likewise, a pair of power leads 19 are provided to be connected to the socket of focusing light 20 to supply the power necessary for maintenance of the light. The fiber optic tube 4 in FIGS. 5 and 6 is shown in position in lens cap 8A with the strobe light 16 extending there across. Likewise, the leads 13 which provide the power to the strobe light 16 from the electronics source.

In use, the lens cap 8A is placed on the lens assembly 1 and the lens assembly is then secured to a camera body by means of a reverse mate 3. The focal length depending on the focal distance of the lens selected. The lens is located an appropriate distance from eye 9 by a focusing adjustment which carries the camera (not shown) but well known in the art, and the picture is taken at which time the stobe light 16 is activated to provide a burst of light which passes out through tube 4.

Because of the fine detail, and the focal length used in close up photography the focusing light provide the necessary illumination on the object, or subject, to obtain a very sharp photograph. While of low intensity the focusing light provides ample illumination for focusing. When all is in focus the strobe light 16 is activated, simulataneously with the camera shutter to provide the burst of light through tube 4 and end 4A to the area being photographed.

As previously discussed, one of the problems with eye photography is the reflective nature of the eye. If proper lighting is not obtain obliteration occurs in the object to be photographed, in this case the iris 15 of the eye. By utilization of an arrangement, as previously described, and because of the nature of the light emitted from the fiber optic cylinder 4, the reflection can be localized in the pupil 21 of the eye. The reflection 22 of the focus light is shown along with the reflection of the strobe light 23 leaving the iris completely free of reflection and obliteration so an excellent photograph can be obtained of the iris of the eye. It has further been found, that by proper orienation of angle A, as shown in FIG. 5 of the focusing light 12 and the angle B of the fiber optic and/or acrylic tube allows the reflection of the focusing light to be seen in the pupil and accordingly the reflection of the stobe light will likewise occur in the pupil giving a high degree of assurance that no obliteration will occur to the iris during the photographic process providing the photographer has properly focused and orientated the camera prior to the photograph.

FIG. 8 is another illustration, as shown, of another arrangement within the scope of the present invention in which the strobe light and focus light are combined. For example, a base 31 is provided, which contains aluminum foil to reflect the strobe light 33 thru the fiber optic sleeve 37. A socket 35 holds sleeve 37 and the incandescent lamp 32 where a stobe light 33 extends through base 31 to provide light to the fiber optic cylinders 37 which surround focusing light socket 35. Leads 38 are provided to provide power to focusing light 32 and leads 39 are provided to supply power to the strobe light 33. In this case the focusing light remains on, as previously described, and when the lens is properly focused, the photograph is snapped with power being supplied by means of leads 39 to the strobe light 33 which then transmits through the fiber optic cylinders 37 to the subject or object to be photographed. In this case, focusing is facilitated to avoid any obliteration because of reflection because the light emitted from the fiber optic cylinder 37 is of small area and travels the same path as light emitted from the focusing light 32, giving some assurance that if the reflection of the focusing light 32 is located in the pupil of the eye then the reflection of the light transmitted from strobe light 33 through cylinders 37 will likewise be located in the pupil of the eye to reduce the likelihood of obliteration of a portion of the iris which is the subject of the photograph.

It will be understood while the present invention has been described with reference to the photography of an eye, other subjects can likewise be utilized where it is necessary to localize the reflection from the strobe light yet provides sufficient like to provide a clear, unobliterated photograph.

It will also be understood that the arrangement shown in the accompaning drawings are but a few examples within the scope of the present invention and that various other arrangements also within the scope of the present invention will occur to those skilled in the art upon reading the disclosure setforth hereinafter.

The invention claimed is:

1. Cap means adapted to be received on a photographic lens having an aperture and a shutter to selectively cover said aperture and generally centrally located in alignment with said lens aperture where said cap includes a focusing light of first intensity and a light flash device to emit selective bursts of light of higher intensity than said focusing light to facilitate macro photographic procedures where said focusing light is adapted to be actuated when said shutter is open wherein said light flash device includes a light transmitting cylinder extending through said cap means with a light source located within said cap means whereby the light generated by said light source passes through said light transmitting cylinder toward an object to be photographed wherein said light transmitting cylinder is located a selected distance from said aperture of said cap means and is disposed with its longitudinal axis at an acute angle relative to a photographic axis extending through said lens shutter and said aperture and directed toward said photographic axis.

2. The invention of claim 1 wherein said light transmitting cylinder is tubular and said focusing light is located to direct light longitudinally through said tubular cylinder.

3. The invention of claim 1 wherein said focusing light is adapted to burn continuously during a photographic process to provide light for focusing said lens.

4. The invention of claim 1 wherein said focusing light and said light transmitting cylinder are located in a socket within said cap and wherein said socket includes light reflecting means to reflect light from said light source to said light transmitting cylinder.

* * * * *